(12) United States Patent
Rusin et al.

(10) Patent No.: US 8,968,291 B2
(45) Date of Patent: *Mar. 3, 2015

(54) DYNAMICALLY MATCHED MICROWAVE ANTENNA FOR TISSUE ABLATION

(71) Applicant: Vivant Medical, Inc., Boulder, CO (US)

(72) Inventors: Christopher T Rusin, Minneapolis, MN (US); Joseph Brannan, Boulder, CO (US)

(73) Assignee: Covidien LP, Mansfield, MA (US)

( * ) Notice: Subject to any disclaimer, the term of this patent is extended or adjusted under 35 U.S.C. 154(b) by 222 days.

This patent is subject to a terminal disclaimer.

(21) Appl. No.: 13/633,256

(22) Filed: Oct. 2, 2012

(65) Prior Publication Data

US 2013/0041365 A1    Feb. 14, 2013

Related U.S. Application Data

(63) Continuation of application No. 12/265,024, filed on Nov. 5, 2008, now Pat. No. 8,280,525.

(60) Provisional application No. 60/988,699, filed on Nov. 16, 2007.

(51) Int. Cl.
*A61B 18/18* (2006.01)
*A61F 2/00* (2006.01)
*A61N 1/06* (2006.01)
*H01Q 1/02* (2006.01)
*H01Q 9/30* (2006.01)

(52) U.S. Cl.
CPC ............. *A61B 18/18* (2013.01); *A61B 18/1815* (2013.01); *H01Q 1/02* (2013.01); *H01Q 9/30* (2013.01)

USPC .............................. 606/33; 607/154; 607/156

(58) Field of Classification Search
CPC .......................... A61B 18/18; A61B 18/1815
USPC ............................. 606/27–52; 607/115–156
See application file for complete search history.

(56) References Cited

U.S. PATENT DOCUMENTS 3,631,363 A    12/1971 Miller
4,397,313 A    8/1983 Vaguine
4,462,412 A    7/1984 Turner
(Continued)

FOREIGN PATENT DOCUMENTS

DE    390937    3/1924
DE    1099658   2/1961
(Continued)

OTHER PUBLICATIONS

U.S. Appl. No. 08/483,742, filed Jun. 7, 1995, Roger A. Stern.
(Continued)

*Primary Examiner* — Jaymi Della
*Assistant Examiner* — Khadijeh Vahdat

(57) ABSTRACT

A microwave ablation probe for providing microwave energy to tissue is disclosed. The probe includes a feedline having an inner conductor, a secondary inner conductor, an insulating spacer, and an outer conductor. The inner conductor is slidably disposed within the secondary inner conductor. The feedline also includes a radiating portion having an extruded portion of the inner conductor centrally disposed therein, wherein longitudinal movement of the inner conductor relative to the feedline tunes the radiating portion.

11 Claims, 2 Drawing Sheets

(56) References Cited

U.S. PATENT DOCUMENTS

| | | |
|---|---|---|
| 4,572,190 A | 2/1986 | Azam et al. |
| 4,798,215 A | 1/1989 | Turner |
| 5,057,106 A | 10/1991 | Kasevich et al. |
| 5,097,844 A | 3/1992 | Turner |
| 5,188,122 A | 2/1993 | Phipps et al. |
| 5,246,438 A | 9/1993 | Langberg |
| 5,248,312 A | 9/1993 | Langberg |
| 5,275,597 A | 1/1994 | Higgins et al. |
| 5,300,068 A | 4/1994 | Rosar et al. |
| 5,364,392 A | 11/1994 | Warner et al. |
| 5,370,644 A | 12/1994 | Langberg |
| 5,405,346 A | 4/1995 | Grundy et al. |
| 5,417,210 A | 5/1995 | Funda et al. |
| 5,558,672 A | 9/1996 | Edwards et al. |
| 5,662,647 A * | 9/1997 | Crow et al. .................. 606/41 |
| 5,683,382 A | 11/1997 | Lenihan et al. |
| 5,688,269 A | 11/1997 | Newton et al. |
| 5,693,082 A | 12/1997 | Warner et al. |
| 5,776,176 A | 7/1998 | Rudie |
| 5,800,494 A | 9/1998 | Campbell et al. |
| 5,807,392 A * | 9/1998 | Eggers .......................... 606/31 |
| 5,861,021 A | 1/1999 | Thome et al. |
| 5,902,251 A | 5/1999 | vanHooydonk |
| 5,931,807 A | 8/1999 | McClure et al. |
| 5,957,969 A | 9/1999 | Warner et al. |
| 6,019,757 A | 2/2000 | Scheldrup |
| 6,031,375 A | 2/2000 | Atalar et al. |
| 6,165,172 A * | 12/2000 | Farley et al. .................. 606/33 |
| 6,233,490 B1 * | 5/2001 | Kasevich ...................... 607/101 |
| 6,287,302 B1 * | 9/2001 | Berube .......................... 606/33 |
| 6,306,132 B1 | 10/2001 | Moorman et al. |
| 6,325,796 B1 | 12/2001 | Berube et al. |
| 6,347,251 B1 | 2/2002 | Deng |
| 6,375,606 B1 | 4/2002 | Garibaldi et al. |
| 6,383,183 B1 | 5/2002 | Sekino et al. |
| 6,398,781 B1 | 6/2002 | Goble et al. |
| 6,451,015 B1 | 9/2002 | Rittman, III |
| 6,471,696 B1 | 10/2002 | Berube et al. |
| 6,496,736 B1 | 12/2002 | Carl et al. |
| 6,496,738 B2 | 12/2002 | Carr |
| 6,508,815 B1 | 1/2003 | Strul et al. |
| 6,527,768 B2 | 3/2003 | Berube |
| 6,582,427 B1 | 6/2003 | Goble et al. |
| 6,603,994 B2 | 8/2003 | Wallace et al. |
| 6,699,241 B2 | 3/2004 | Rappaport et al. |
| 6,725,080 B2 | 4/2004 | Melkent et al. |
| 6,758,846 B2 * | 7/2004 | Goble et al. .................. 606/41 |
| 7,070,595 B2 | 7/2006 | Ormsby et al. |
| 7,101,369 B2 | 9/2006 | van der Welde |
| 7,194,297 B2 | 3/2007 | Talpade et al. |
| 7,226,446 B1 | 6/2007 | Mody et al. |
| 7,393,352 B2 | 7/2008 | Berube |
| 7,439,736 B2 | 10/2008 | Meaney et al. |
| 7,467,015 B2 | 12/2008 | van der Weide |
| 7,538,038 B2 | 5/2009 | Matsushita |
| 7,565,207 B2 | 7/2009 | Turner et al. |
| 7,642,451 B2 | 1/2010 | Bonn |
| 8,035,570 B2 | 10/2011 | Prakash et al. |
| 8,059,059 B2 | 11/2011 | Bonn |
| 8,118,808 B2 | 2/2012 | Smith et al. |
| 8,182,480 B2 | 5/2012 | Huseman |
| 8,192,427 B2 | 6/2012 | Buysse |
| 8,197,473 B2 | 6/2012 | Rossetto et al. |
| 8,202,270 B2 | 6/2012 | Rossetto et al. |
| 8,211,098 B2 | 7/2012 | Paulus |
| 8,211,099 B2 | 7/2012 | Buysse et al. |
| 8,221,418 B2 | 7/2012 | Prakash et al. |
| 8,235,981 B2 | 8/2012 | Prakash et al. |
| 8,246,614 B2 | 8/2012 | DeCarlo |
| 8,251,987 B2 | 8/2012 | Willyard |
| 8,262,703 B2 | 9/2012 | Prakash et al. |
| 8,292,880 B2 | 10/2012 | Prakash et al. |
| 8,292,881 B2 | 10/2012 | Brannan et al. |
| 8,343,149 B2 | 1/2013 | Rossetto et al. |
| 2002/0022836 A1 | 2/2002 | Goble et al. |
| 2002/0087151 A1 | 7/2002 | Mody et al. |
| 2003/0032951 A1 | 2/2003 | Rittman, III |
| 2003/0065317 A1 | 4/2003 | Rudie et al. |
| 2003/0088242 A1 * | 5/2003 | Prakash et al. .................. 606/33 |
| 2004/0049254 A1 | 3/2004 | Longo |
| 2004/0097805 A1 | 5/2004 | Verard et al. |
| 2004/0242992 A1 | 12/2004 | Hareyama |
| 2005/0015081 A1 * | 1/2005 | Turovskiy et al. .............. 606/33 |
| 2005/0165389 A1 * | 7/2005 | Swain et al. .................... 606/27 |
| 2005/0222558 A1 | 10/2005 | Baxter et al. |
| 2005/0245919 A1 | 11/2005 | Van der Welde |
| 2006/0189973 A1 | 8/2006 | Van der Weide |
| 2006/0287649 A1 | 12/2006 | Ormsby et al. |
| 2006/0293652 A1 | 12/2006 | van der Weide |
| 2007/0016181 A1 | 1/2007 | Van der Weide et al. |
| 2007/0185554 A1 | 8/2007 | Appling et al. |
| 2007/0203480 A1 | 8/2007 | Mody et al. |
| 2007/0265609 A1 | 11/2007 | Thapliyal et al. |
| 2007/0265610 A1 | 11/2007 | Thapliyal et al. |
| 2007/0282320 A1 | 12/2007 | Buysse et al. |
| 2009/0187180 A1 | 7/2009 | Brannan |
| 2009/0192510 A1 | 7/2009 | Bahney |
| 2009/0198227 A1 | 8/2009 | Prakash |
| 2009/0222002 A1 | 9/2009 | Bonn et al. |
| 2009/0248005 A1 | 10/2009 | Rusin et al. |
| 2009/0248006 A1 | 10/2009 | Paulus et al. |
| 2009/0306652 A1 | 12/2009 | Buysse et al. |
| 2010/0030206 A1 | 2/2010 | Brannan et al. |
| 2010/0030208 A1 | 2/2010 | Manley |
| 2010/0030210 A1 | 2/2010 | Paulus |
| 2010/0045558 A1 | 2/2010 | Rossetto |
| 2010/0045559 A1 | 2/2010 | Rossetto |
| 2010/0057070 A1 | 3/2010 | Behnke et al. |
| 2010/0076422 A1 | 3/2010 | Podhajsky |
| 2010/0087808 A1 | 4/2010 | Paulus |
| 2010/0094272 A1 | 4/2010 | Rossetto et al. |
| 2010/0094273 A1 | 4/2010 | Rossetto et al. |
| 2010/0097284 A1 | 4/2010 | Brannan et al. |
| 2010/0256624 A1 | 10/2010 | Brannan et al. |
| 2010/0262134 A1 | 10/2010 | Jensen et al. |
| 2010/0286681 A1 | 11/2010 | Podhajsky |
| 2010/0286682 A1 | 11/2010 | Podhajsky |
| 2010/0286683 A1 | 11/2010 | Podhajsky |
| 2010/0305560 A1 | 12/2010 | Peterson |

FOREIGN PATENT DOCUMENTS

| | | |
|---|---|---|
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2415263 | 10/1975 |
| DE | 2429021 | 1/1976 |
| DE | 2460481 | 6/1976 |
| DE | 2602517 | 7/1976 |
| DE | 2504280 | 8/1976 |
| DE | 2627679 | 1/1977 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 8712328 | 3/1988 |
| DE | 3711511 | 6/1988 |
| DE | 3904558 | 8/1990 |
| DE | 4238263 | 5/1993 |
| DE | 4339049 | 5/1995 |
| DE | 19608716 | 4/1997 |
| DE | 19751106 | 5/1998 |
| DE | 19717411 | 11/1998 |
| DE | 19751108 | 5/1999 |
| DE | 19801173 | 7/1999 |

(56) References Cited

FOREIGN PATENT DOCUMENTS

| | | |
|---|---|---|
| DE | 19848540 | 5/2000 |
| DE | 10224154 | 12/2003 |
| DE | 10328514 | 3/2005 |
| DE | 102004022206 | 12/2005 |
| DE | 202005015147 | 3/2006 |
| EP | 0 246 350 | 11/1987 |
| EP | 0 481 685 | 4/1992 |
| EP | 0 521 264 | 1/1993 |
| EP | 0 541 930 | 5/1993 |
| EP | 0 556 705 | 8/1993 |
| EP | 0 558 429 | 9/1993 |
| EP | 0 572 131 | 12/1993 |
| EP | 0 836 868 | 4/1998 |
| EP | 1 034 748 | 9/2000 |
| EP | 1 159 926 | 5/2001 |
| EP | 1 278 007 | 1/2003 |
| EP | 1186274 | 4/2006 |
| EP | 1 810 627 | 7/2007 |
| FR | 179 607 | 11/1906 |
| FR | 1 275 415 | 9/1960 |
| FR | 1 347 865 | 11/1963 |
| FR | 2 276 027 | 6/1974 |
| FR | 2 235 669 | 1/1975 |
| FR | 2 313 708 | 12/1976 |
| FR | 2 502 935 | 10/1982 |
| FR | 2 517 953 | 6/1983 |
| FR | 2 573 301 | 11/1984 |
| FR | 2 862 813 | 5/2005 |
| FR | 2 864 439 | 7/2005 |
| JP | 5-5106 | 1/1993 |
| JP | 05-40112 | 2/1993 |
| JP | 06343644 | 12/1994 |
| JP | 07265328 | 10/1995 |
| JP | 08056955 | 3/1996 |
| JP | 08252263 | 10/1996 |
| JP | 09010223 | 1/1997 |
| JP | 11244298 | 9/1999 |
| JP | 2000342599 | 12/2000 |
| JP | 2000350732 | 12/2000 |
| JP | 2001008944 | 1/2001 |
| JP | 2001029356 | 2/2001 |
| JP | 2001128990 | 5/2001 |
| SU | 166452 | 11/1964 |
| SU | 401367 | 11/1974 |
| SU | 727201 | 4/1980 |
| WO | WO97/41924 | 11/1997 |
| WO | WO97/43971 | 11/1997 |
| WO | WO97/48449 | 12/1997 |
| WO | WO97/48451 | 12/1997 |
| WO | WO99/51158 | 10/1999 |
| WO | WO00/48672 | 8/2000 |
| WO | WO00/49957 | 8/2000 |
| WO | WO00/51513 | 9/2000 |
| WO | WO00/53112 | 9/2000 |
| WO | WO01/01847 | 1/2001 |
| WO | WO01/74252 | 10/2001 |
| WO | WO02/45790 | 6/2002 |
| WO | WO02/061880 | 8/2002 |
| WO | WO03/088858 | 10/2003 |
| WO | WO2004/112628 | 12/2004 |
| WO | WO2005/011049 | 2/2005 |
| WO | WO2005/016119 | 2/2005 |
| WO | WO2007/112081 | 10/2007 |

OTHER PUBLICATIONS

U.S. Appl. No. 08/136,098, filed Oct. 14, 1993, Roger A. Stern.
International Search Report EP08/019920 dated Mar. 27, 2009.
Esterline Product Literature, "Light Key: Visualize a Virtual Keyboard. One With No Moving Parts", Nov. 1, 2003; 4 pages.
H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.
European Search Report EP 08011282 dated Aug. 14, 2009.
European Search Report EP 04778192.7 dated Jul. 1, 2009.
European Search Report EP 05810523 dated Jan. 29, 2009.
European Search Report EP 08011705 dated Aug. 20, 2009.
European Search Report EP 08012829.1 dated Oct. 29, 2008.
European Search Report EP 08019920.1 dated Mar. 27, 2009.
European Search Report EP 08169973.8 dated Apr. 6, 2009.
European Search Report EP 09156861.8 dated Aug. 4, 2009.
European Search Report EP 09161502.1 dated Sep. 2, 2009.
European Search Report EP 09166708 dated Oct. 15, 2009.
International Search Report PCT/US05/36168 dated Aug. 28, 2006.
International Search Report PCT/US08/052460 dated Apr. 24, 2008.
International Search Report PCT/US09/31658 dated Mar. 11, 2009.
Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.
Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product instructions), 2 pgs.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok.TM. Breast Lesion Needle/Wire Localizer, Namic.RTM. Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.
Anonymous. Ground Cannulae, ISPG, New Milford, CT, (Advertisement) one page, Jul. 19, 2000.
B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Durney et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyrus PlasmaKinetic Sealer and the Valleylab LigaSure.TM. Device in the Hemostasis of Small, Medium, and Large-Sized Arteries" Carolinas Laparoscopic and Advanced Surgery Program, Carolinas Medical Center, Charlotte, NC 2003.
Carus et al., "Initial Experience With the LigaSure.TM. Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 941n Biologic Effects of Nonionizing Electromagnetic Fields, CRC Press, Inc., pp. 1424-1428.
Chung et al., "Clinical Experience of Sutureless Closed Hemorrhoidectomy with LigaSure.TM." Diseases of the Colon & Rectum, vol. 46, No. 1, Jan. 2003.

(56) References Cited

OTHER PUBLICATIONS

Cosman et al., "Radiofrequency Lesion Generation and its Effect on Tissue Impedence", Applied Neurophysiology, 51:230-242, 1988.

Cosman et al., "Theoretical Aspects of Radiofrequency Lesions in the Dorsal Root Entry Zone" Neurosurgery 15:(1984), pp. 945-950.

Cosman et al., "Methods of Making Nervous System Lesions" in William RH, Rengachary SS (eds): Neurosurgery, New York: McGraw Hill, vol. 111, (1984), pp. 2490-2499.

Crawford et al., "Use of the LigaSure.TM. Vessel Sealing System in Urologic Cancer Surger" Grand Rounds in Urology 1999, vol. 1, Issue 4, pp. 10-17.

Dulemba et al., "Use of a Bipolar Electrothermal Vessel Sealer in Laparoscopically Assisted Vaginal Hysterectomy" Sales/Product Literature; Jan. 2004.

E. David Crawford, "Evaluation of a New Vessel Sealing Device in Urologic Cancer Surgery" Sales/Product Literature 2000.

E. David Crawford, "Use of a Novel Vessel Sealing Technology in Management of the Dorsal Veinous Complex" Sales/Product Literature 2000.

Esterline Product Literature, "Light Key: Visualize a Virtual Keyboard. One With no Moving Parts", 4 pages.

Esterline, "Light Key Projection Keyboard" 2004 Advanced Input Systems, located at: <http://www.advanced-input.com/lightkey> last visited on Feb. 10, 2005.

Geddes et al., "The Measurement of Physiologic Events by Electrical Impedence" Am. J. Ml, Jan. Mar. 1964, pp. 16-27.

Goldberg et al., "Image-guided Radiofrequency Tumor Ablation: Challenges and Opportunities—Part I", (2001) J Vasc. Interv. Radial, vol. 12, pp. 1021-1032.

Goldberg et al., "Tissue Ablation with Radiofrequency: Effect of Probe Size, Gauge, Duration, and Temperature on Lesion Volume" Acad Radio (1995) vol. 2, No. 5, pp. 399-404.

Heniford et al., "Initial Results with an Electrothermal Bipolar Vessel Sealer" Surgical Endoscopy (2001) 15:799-801.

Herman et al., "Laparoscopic Intestinal Resection With the LigaSure. TM. Vessel Sealing System: A Case Report" Innovations That Work, Feb. 2002.

Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.

Johnson et al., "Evaluation of a Bipolar Electrothermal Vessel Sealing Device in Hemorrhoidectomy" Sales/Product Literature, Jan. 2004.

Jarrett et al., "Use of the LigaSure.TM. Vessel Sealing System for Peri-Hilar Vessels in Laparoscopic Nephrectomy" Sales/Product Literature 2000.

Johnson, "Evaluation of the LigaSure.TM. Vessel Sealing System in Hemorrhoidectomy" American College of Surgeons (ACS) Clinic La Congress Poster (2000).

Johnson, "Use of the LigaSure.TM. Vessel Sealing System in Bloodless Hemorrhoidectomy" Innovations That Work, Mar. 2000.

K. Ogata, Modern Control Engineering, Prentice-Hall, Englewood Cliffs, N.J., 1970.

Kennedy et al., "High-burst-strength, feedback-controlled bipolar vessel sealing" Surgical Endoscopy (1998) 12: 876-878.

Kopans, D.B. et al., (Nov. 1985) "Spring Hookwire Breast Lesion Localizer: Use with Rigid-Compression. Mammographic Systems," Radiology 157(2):537-538.

Koyle et al., "Laparoscopic Palomo Varicocele Ligation in Children and Adolescents" Pediatric Endosurgery & Innovative Techniques, vol. 6, No. 1, 2002.

LigaSure.TM. Vessel Sealing System, the Seal of Confidence in General , Gynecologic, Urologic, and Laparaoscopic Surgery, Sales/Product Literature, Jan. 2004.

Livraghi et al., (1995) "Saline-enhanced RF Tissue Ablation in the Treatment of Liver Metastases", Radiology, pp. 205-210.

Lyndon B. Johnson Space Center, Houston, Texas, "Compact Directional Microwave Antenna for Localized Heating," NASA Tech Briefs, Mar. 2008.

M. A. Astrahan, "A Localized Current Field Hyperthermia System for Use with 192-Iridium Interstitial Implants" Medical Physics. 9(3), May/Jun. 1982.

Magdy F. Iskander et al., "Design Optimization of Interstitial Antennas", IEEE Transactions on Biomedical Engineering, vol. 36, No. 2, Feb. 1989, pp. 238-246.

McGahan et al., (1995) "Percutaneous Ultrasound-guided Radiofrequency Electrocautery Ablation of Prostate Tissue in Dogs", Acad Radio!, vol. 2, No. 1: pp. 61-65.

McLellan et al., "Vessel Sealing for Hemostasis During Pelvic Surgery" Int'l Federation of Gynecology and Obstetrics Figo World Congress 2000, Washington, DC.

Joseph G. Andriole M.D. et al., "Biopsy Needle Characteristics Assessed in the Laboratory", Radiology 148: 659-682, Sep. 1983.

Joseph Ortenberg, "LigaSure.TM. System Used in Laparoscopic 1st and 2nd Stage Orchiopexy" Innovations That Work, Nov. 2002.

MDTech product literature (Mar. 2000) I'D Wire: product description, 1 page.

MDTech product literature (Dec. 1999) "FlexStrand": product description, 1 page.

Medtrex Brochure "The O.R. Pro 300" 1 page, Sep. 1998.

Michael Choti, "Abdominoperineal Resection with the LigaSure. TM. Vessel Sealing System and LigaSure.TM. Atlas 20 cm Open Instrument" Innovations That Work, Jun. 2003.

Muller et al., "Extended Left Hemicolectomy Using the LigaSure. TM. Vessel Sealing System" Innovations That Work, LJ, Sep. 1999.

Murakami, R. et al., (1995). "Treatment of Hepatocellular Carcinoma: Value of Percutaneous Microwave Coagulation," American Journal of Radiology (AJR) 164:1159-1164.

Ni Wei at al., "A Signal Processing Method for the Coriolis Mass Flowmeter Based on a Normalized . . . " Journal of Applied Sciences Yingyong Kexue Xuebao, Shangha CN, vol. 23, No. 2:(Mar. 2005); pp. 160-184.

Ogden, "Goertzel Alternative to the Fourier Transform" Jun. 1993 pp. 485-487 Electronics World; Reed Business Publishing, Sutton, Surrey, BG, vol. 99, No. 9, 1687.

Olsson M.D. et al., "Radical Cystectomy in Females" Current Surgical Techniques in Urology, vol. 14, Issue 3, 2001.

Organ, L W., "Electrophysiologic Principles of Radiofrequency Lesion Making" Appl. Neurophysiol, vol. 39: pp. 69-76 (1976/1977).

P.R. Stauffer et al., "Interstitial Heating Technologies", Thermoradiotheray and Thermochemotherapy (1995) vol. I, Biology, Physiology, Physics, pp. 279-320.

Palazzo et al., "Randomized clinical trial of LigaSure.™. versus open haemorrhoidectomy" British Journal of Surgery 2002,89,154-157 "Innovations in Electrosurgery" Sales/Product Literature; Dec. 31, 2000.

Paul G. Horgan, "A Novel Technique for Parenchymal Division During Hepatectomy" The American Journal of Surgery, vol. 181, No. 3, Apr. 2001, pp. 236-237.

Peterson et al., "Comparison of Healing Process Following Ligation with Sutures and Bipolar Vessel Sealing" Surgical Technology International (2001).

R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.

Valleylab Brochure, "Reducing Needlestick Injuries in the Operating Room" 1 page, Mar. 2001.

Reidenbach, (1995) "First Experimental Results with Special Applicators for High-Frequency Interstitial Thermotherapy", Society Minimally Invasive Therapy, 4(Suppl 1):40 (Abstr).

Richard Wolf Medical Instruments Corp. Brochure, "Kleppinger Bipolar Forceps & Bipolar Generator" 3 pages, Jan. 1989.

Rothenberg et al., "Use of the LigaSure.TM. Vessel Sealing System in Minimally Invasive Surgery in Children" Int'l Pediatric Endosurgery Group (1 PEG) 2000.

Sengupta et al., "Use of a Computer-Controlled Bipolar Diathermy System in Radical Prostatectomies and Other Open Urological Surgery" ANZ Journal of Surgery (2001) 71.9 pp. 538-540.

Sigel et al., "The Mechanism of Blood Vessel Closure by High Frequency Electrocoagulation" Surgery Gynecology & Obstetrics, Oct. 1965 pp. 823-831.

(56) References Cited

OTHER PUBLICATIONS

Solbiati et al., (2001) "Percutaneous Radio-frequency Ablation of Hepatic Metastases from Colorectal Cancer: Long-term Results in 117 Patients", Radiology, vol. 221, pp. 159-166.
Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.
Sugita et al., "Bipolar Coagulator with Automatic Thermocontrol" J. Neurosurg., vol. 41, Dec. 1944, pp. 777-779.
Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 410-415, 1997.
T. Seki et al., (1994) "Ultrasonically Guided Percutaneous Microwave Coagulation Therapy for Small Hepatocellular Carcinoma," Cancer 74(3):817 825.
S. Humphries Jr. et al., "Finite Element Codes to Model Electrical Heating and Non.cndot.LInear Thermal Transport in Biological Media", Proc. ASME HTD-355, 131 (1997).
Urologix, Inc.—Medical Professionals: Targis.TM. Technology (Date Unknown). "Overcoming the Challenge" located at: <http://www.urologix.com!medicaUtechnology.html > last visited on Apr. 27, 2001, 3 pages.
Urrutia et al., (1988). "Retractable-Barb Needle for Breast Lesion Localization: Use in 60 Cases," Radiology 169(3):845-847.
Valleylab Brochure, "Valleylab Electroshield Monitoring System" 2 pages, Nov. 1995.
ValleyLab Brochure, "Electosurgery: A Historical Overview", Innovations in Electrosurgery, 1999.
Valifors et al., "Automatically Controlled Bipolar Electrocoagulation—'COA-COMP'" Neurosurgical Review 7:2-3 (1984) pp. 187-190.
W. Scott Helton, "LigaSure.TM. Vessel Sealing System: Revolutionary Hemostasis Product for General Surgery" Sales/Product Literature 1999.
Wald et al., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
European Search Report EP 03721482 dated Feb. 6, 2006.
European Search Report EP 04009964 dated Jul. 28, 2004.
European Search Report EP 04013772 dated Apr. 11, 2005.
European Search Report EP 04015980 dated Nov. 3, 2004.
European Search Report EP 04015981.6 dated Oct. 25, 2004.
European Search Report EP 04027314 dated Mar. 31, 2005.
European Search Report EP 04027479 dated Mar. 17, 2005.
European Search Report EP 04027705 dated Feb. 10, 2005.
European Search Report EP 04710258 dated Oct. 15, 2004.
European Search Report EP 04752343.6 dated Jul. 31, 2007.
European Search Report EP 05002027.0 dated May 12, 2005.
European Search Report EP 05002769.7 dated Jun. 19, 2006.
European Search Report EP 05013463.4 dated Oct. 7, 2005.
European Search Report EP 05013895 dated Oct. 21, 2005.
European Search Report EP 05014156.3 dated Jan. 4, 2006.
European Search Report EP 05016399 dated Jan. 13, 2006.
European Search Report EP 05017281 dated Nov. 24, 2005.
European Search Report EP 05019130.3 dated Oct. 27, 2005.
European Search Report EP 05019882 dated Feb. 16, 2006.
European Search Report EP 05020665.5 dated Feb. 27, 2006.
European Search Report EP 05020666.3 dated Feb. 27, 2006.
European Search Report EP 05021025.1 dated Mar. 13, 2006.
European Search Report EP 05021197.8 dated Feb. 20, 2006.
European Search Report EP 05021777 dated Feb. 23, 2006.
European Search Report EP 05021779.3 dated Feb. 2, 2006.
European Search Report EP 05021780.1 dated Feb. 23, 2006.
European Search Report EP 05021935 dated Jan. 27, 2006.
European Search Report EP 05021936.9 dated Feb. 6, 2006.
European Search Report EP 05021937.7 dated Jan. 23, 2006.
European Search Report EP 05021939 dated Jan. 27, 2006.
European Search Report EP 05021944.3 dated Jan. 25, 2006.
European Search Report EP 05022350.2 dated Jan. 30, 2006.
European Search Report EP 05023017.6 dated Feb. 24, 2006.
European Search Report EP 05025423.4 dated Jan. 19, 2007.
European Search Report EP 05025424 dated Jan. 30, 2007.
European Search Report EP 06000708.5 dated May 15, 2006.
European Search Report EP 06002279.5 dated Mar. 30, 2006.
European Search Report EP 06005185.1 dated May 10, 2006.
European Search Report EP 06005540 dated Sep. 24, 2007.
European Search Report EP 06006717.0 dated Aug. 11, 2006.
European Search Report EP 06006961 dated Oct. 22, 2007.
European Search Report EP 06006963 dated Jul. 25, 2006.
European Search Report EP 06008779.8 dated Jul. 13, 2006.
European Search Report EP 06009435 dated Jul. 13, 2006.
European Search Report EP 06010499.9 dated Jan. 29, 2008.
European Search Report EP 06014461.5 dated Oct. 31, 2006.
European Search Report EP 06018206.0 dated Oct. 20, 2006.
European Search Report EP 06019768 dated Jan. 17, 2007.
European Search Report EP 06020574.7 dated Oct. 2, 2007.
European Search Report EP 06020583.8 dated Feb. 7, 2007.
European Search Report EP 06020584.6 dated Feb. 1, 2007.
European Search Report EP 06020756.0 dated Feb. 16, 2007.
European Search Report EP 06022028.2 dated Feb. 13, 2007.
European Search Report EP 06023756.7 dated Feb. 21, 2008.
European Search Report EP 06024122.1 dated Apr. 16, 2007.
European Search Report EP 06024123.9 dated Mar. 6, 2007.
European Search Report EP 06025700.3 dated Apr. 12, 2007.
European Search Report EP 07000885.9 dated May 15, 2007.
European Search Report EP 07001480.8 dated Apr. 19, 2007.
European Search Report EP 07001481.6 dated May 2, 2007.
European Search Report EP 07001485.7 dated May 23, 2007.
European Search Report EP 07001488.1 dated Jun. 5, 2007.
European Search Report EP 07001489.9 dated Dec. 20, 2007.
European Search Report EP 07001491 dated Jun. 6, 2007.
European Search Report EP 07001527.6 dated May 18, 2007.
European Search Report EP 07007783.9 dated Aug. 14, 2007.
European Search Report EP 07008207.8 dated Sep. 13, 2007.
European Search Report EP 07009026.1 dated Oct. 8, 2007.
European Search Report EP 07009028 dated Jul. 16, 2007.
European Search Report EP 07009029.5 dated Jul. 20, 2007.
European Search Report EP 07009321.6 dated Aug. 28, 2007.
European Search Report EP 07009322.4 dated Jan. 14, 2008.
European Search Report EP 07010672.9 dated Oct. 16, 2007.
European Search Report EP 07010673.7 dated Oct. 5, 2007.
European Search Report EP 07013779.9 dated Oct. 26, 2007.
European Search Report EP 07015191.5 dated Jan. 23, 2007.
European Search Report EP 07015601.3 dated Jan. 4, 2007.
European Search Report EP 07015602.1 dated Dec. 20, 2007.
European Search Report EP 07018375.1 dated Jan. 8, 2008.
European Search Report EP 07018821 dated Jan. 14, 2008.
European Search Report EP 07019173.9 dated Feb. 12, 2008.
European Search Report EP 07019174.7 dated Jan. 29, 2008.
European Search Report EP 07019178.8 dated Feb. 12, 2008.
European Search Report EP 07020283.3 dated Feb. 5, 2008.
European Search Report EP 07253835.8 dated Dec. 20, 2007.
European Search Report EP 08001019 dated Sep. 23, 2008.
European Search Report EP 08004975 dated Jul. 24, 2008.
European Search Report EP 08006731.7 dated Jul. 29, 2008.
European Search Report EP 08006733 dated Jul. 7, 2008.
European Search Report EP 08006734.1 dated Aug. 18, 2008.
European Search Report EP 08006735.8 dated Jan. 8, 2009.
European Search Report EP 08015842 dated Dec. 5, 2008.
European Search Report EP 98300964.8 dated Dec. 13, 2000.
European Search Report EP 98944778 dated Nov. 7, 2000.
European Search Report EP 98958575.7 dated Oct. 29, 2002.
International Search Report PCT/US01/11218 dated Aug. 14, 2001.
International Search Report PCT/US01/11224 dated Nov. 13, 2001.
International Search Report PCT/US01/11340 dated Aug. 16, 2001.
International Search Report PCT/US01/11420 dated Oct. 16, 2001.
International Search Report PCT/US02/01890 dated Jul. 25, 2002.
International Search Report PCT/US02/11100 dated Jul. 16, 2002.
International Search Report PCT/US03/09483 dated Aug. 13, 2003.
International Search Report PCT/US03/22900 dated Dec. 2, 2003.

(56) References Cited

OTHER PUBLICATIONS

International Search Report PCT/US03/37110 dated Jul. 25, 2005.
International Search Report PCT/US03/37111 dated Jul. 28, 2004.
International Search Report PCT/US03/37310 dated Aug. 13, 2004.
International Search Report PCT/US04/04685 dated Aug. 27, 2004.
International Search Report PCT/US04/13273 dated Dec. 15, 2004.
International Search Report PCT/US04/15311 dated Jan. 12, 2004.
International Search Report PCT/US98/18640 dated Jan. 29, 1998.
International Search Report PCT/US98/23950 dated Jan. 14, 1998.
International Search Report PCT/US99/24869 dated Feb. 11, 2000.
International Search Report EP10161722 dated Jun. 16, 2010.
European Search Report for European Application No. 11185926.0 dated Jan. 23, 2012.

* cited by examiner

DYNAMICALLY MATCHED MICROWAVE ANTENNA FOR TISSUE ABLATION

CROSS-REFERENCE TO RELATED APPLICATION

The present application is a continuation of U.S. application Ser. No. 12/265,024 filed on Nov. 5, 2008, now U.S. Pat. No. 8,280,525, which claims the benefit of and priority to U.S. Provisional Application Ser. No. 60/988,699 filed on Nov. 16, 2007, the entirety of each of which is incorporated by reference herein.

BACKGROUND

1. Technical Field

The present disclosure relates generally to microwave applicator probes used in tissue ablation procedures. More particularly, the present disclosure is directed to a microwave probe that can be tuned during ablation procedures to obtain a desired impedance match.

2. Background of Related Art

Treatment of certain diseases requires destruction of malignant tissue growths (e.g., tumors). It is known that tumor cells denature at elevated temperatures that are slightly lower than temperatures injurious to surrounding healthy cells. Therefore, known treatment methods, such as hyperthermia therapy, heat tumor cells to temperatures above 41° C., while maintaining adjacent healthy cells at lower temperatures to avoid irreversible cell damage. Such methods involve applying electromagnetic radiation to heat tissue and include ablation and coagulation of tissue. In particular, microwave energy is used to coagulate and/or ablate tissue to denature or kill the cancerous cells.

Microwave energy is applied via microwave ablation antenna probes which penetrate tissue to reach tumors. There are several types of microwave probes, such as monopole, dipole, and helical. In monopole and dipole probes, microwave energy radiates perpendicularly from the axis of the conductor. Monopole probe (e.g., antenna) includes a single, elongated microwave conductor surrounded by a dielectric sleeve, having a conductor exposed at the end of the probe. Dipole probes have a coaxial construction including an inner conductor and an outer conductor separated by a dielectric portion. More specifically, dipole microwave antennas have a long, thin inner conductor which extends along a longitudinal axis of the probe and is surrounded by an outer conductor. In certain variations, a portion or portions of the outer conductor may be selectively removed to provide for more effective outward radiation of energy. This type of microwave probe construction is typically referred to as a "leaky waveguide" or "leaky coaxial" antenna.

In helical probes, microwave energy is directed in a forward direction. This is due to microwave energy radiating perpendicularly from the antenna, which when in helical configuration directs the energy waves in a forward direction. In helical probes the inner conductor is formed in a uniform spiral pattern (e.g., a helix) to provide the required configuration for effective radiation.

Conventional microwave probes have a narrow operational bandwidth, a wavelength range at which optimal operational efficiency is achieved, and hence, are incapable of maintaining a predetermined impedance match between the microwave delivery system (e.g., generator, cable, etc.) and the tissue surrounding the microwave probe. More specifically, as microwave energy is applied to tissue, the dielectric constant of the tissue immediately surrounding the microwave probe decreases as the tissue is cooked. The drop causes the wavelength of the microwave energy being applied to tissue to increase beyond the bandwidth of the probe. As a result, there is a mismatch between the bandwidth of conventional microwave probe and the microwave energy being applied. Thus, narrow band microwave probes may detune as a result of steam generation and phase transformation of the tissue hindering effective energy delivery and dispersion.

SUMMARY

The present disclosure provides for a microwave ablation probe which can be dynamically matched and/or tuned during ablation. As tissue is ablated, the radiating portion of the probe is actively tuned so that an optimal impedance match is achieved for a desired procedure. This is accomplished by adjusting the shape, size and/or dielectric properties of the components of the probe (e.g., adjusting the length of the conductors, insulating layers, and the like). In monopole and/or dipole antennas, the length of an inner conductor is adjusted to create a more efficient radiator. In dipole antennas, the length of the outer and inner conductors is adjusted such that a predetermined wavelength distance at the radiating portion is maintained despite frequency changes (e.g., inner and outer conductors being ¼ wavelength long to maintain balanced behavior of a ¼ wavelength dipole). In another embodiment, dielectric properties of the radiating portion are adjusted by using materials with thermally changing dielectric properties; thus, as the temperature of the tissue and the probe changes during ablation the dielectric properties of the probe are automatically adjusted.

According to one embodiment of the present disclosure a microwave ablation probe for providing microwave energy to tissue is disclosed. The probe includes a feedline having an inner conductor, a secondary inner conductor, an insulating spacer, and an outer conductor. The inner conductor is slidably disposed within the secondary inner conductor. The feedline also includes a radiating portion having an extruded portion of the inner conductor centrally disposed therein, wherein longitudinal movement of the inner conductor relative to the feedline tunes the radiating portion.

According to another embodiment of the present disclosure a microwave ablation probe for providing microwave energy to tissue is disclosed. The probe includes a feedline having an inner conductor, an insulating spacer and an outer conductor, and a radiating portion having an extruded portion of the inner conductor which is centrally disposed therein. The probe also includes a choke disposed around at least a portion of the feedline and configured to confine the microwave energy to the radiating portion. The choke includes a conductive housing having a chamber for storing a cooling dielectric liquid.

According to a further embodiment of the present disclosure a microwave ablation probe for providing microwave energy to tissue is disclosed. The probe includes a feedline having an inner conductor, an insulating spacer and an outer conductor, a radiating portion including a radiating portion including at least a portion of the inner conductor centrally disposed therein. The probe also includes one or more loadings having an electric field-dependent dielectric material, wherein one or more of the dielectric properties of the electric field-dependent dielectric material varies in response to the electric field supplied thereto.

BRIEF DESCRIPTION OF THE DRAWINGS

The above and other aspects, features, and advantages of the present disclosure will become more apparent in light of

BRIEF DESCRIPTION OF THE DRAWINGS the following detailed description when taken in conjunction with the accompanying drawings in which.

DETAILED DESCRIPTION

Particular embodiments of the present disclosure will be described herein below with reference to the accompanying drawings. In the following description, well-known functions or constructions are not described in detail to avoid obscuring the present disclosure in unnecessary detail.

Figure 1:
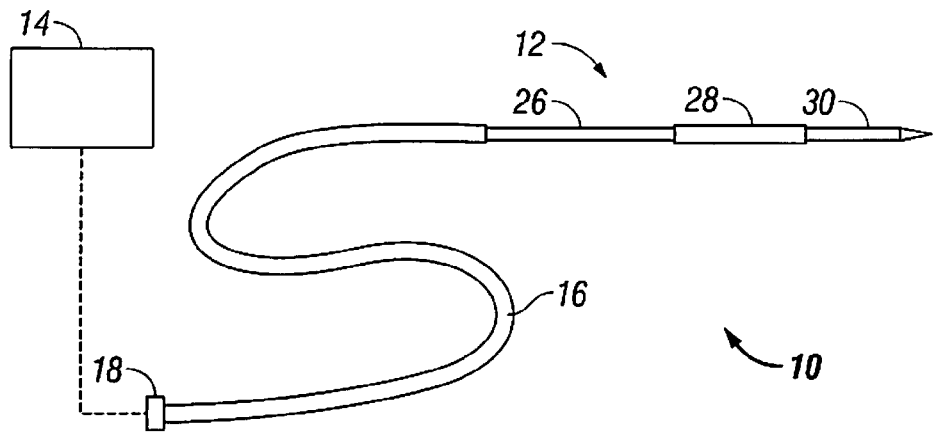
FIG. 1 is a schematic diagram of a microwave ablation system according to the present disclosure.

FIG. 1 shows a microwave ablation system 10 which includes a microwave ablation probe 12 coupled to a microwave generator 14 via a flexible coaxial cable 16 that is coupled to a connector 18 of the generator 14. The generator 14 is configured to provide microwave energy at an operational frequency from about 500 MHz to about 2500 MHz.

During microwave ablation, the probe 12 is inserted into tissue and microwave energy is supplied thereto. As tissue surrounding the probe 12 is ablated, the tissue undergoes desiccation and denaturization which results in a drop of the effective dielectric constant of the tissue. The drop in the effective dielectric constant, in turn, lengthens the wavelength of the microwave energy. Since the frequency is held constant during ablation, the increase in the wavelength results in the increase of the operational frequency. At the outset the probe 12 is at an initial match point—a predetermined operational frequency that increases to a higher frequency as the ablation continues. Thus, to maintain an impedance match between the probe 12 and the generator 14, the radiating properties of the probe 12 are dynamically adjusted throughout the procedure. This is accomplished by modifying the geometry and/or the dielectric properties of the probe 12.

Figure 2:
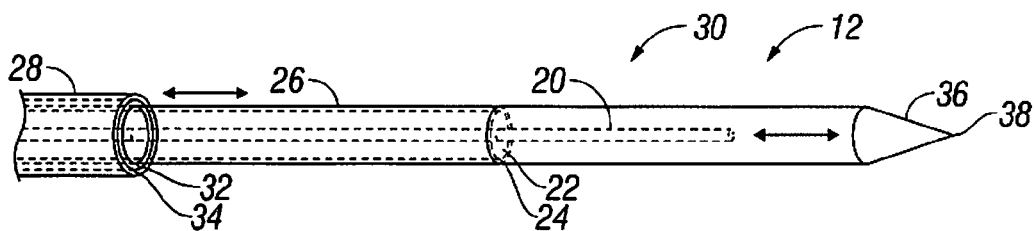
FIG. 2 is a perspective cross-sectional view of a microwave ablation probe according to the present disclosure.

FIG. 2 shows one embodiment of the probe 12 including a feedline 26, a choke 28 and an adjustable radiating portion 30. The feedline 26 extends between the distal end of the probe 12 where the feedline 26 is coupled to the cable 16, to the radiating portion 30. The feedline 26 is constructed from a coaxial cable having an inner conductor 20 (e.g., wire) surrounded by an insulating spacer 22 which is then surrounded by an outer conductor 24 (e.g., cylindrical conducting sheath). In one embodiment, the feedline 26 may have a diameter of 0.085 inches and the insulating spacer 22 may have a dielectric constant of 1.7.

The feedline 26 may be flexible or semi-rigid and may be of variable length from a proximal end of the radiating portion 30 to a distal end of the cable 16 ranging from about 1 to about 10 inches. The inner conductor 20 and the outer conductor 24 may be constructed from a variety of metals and alloys, such as copper, gold, stainless steel, and the like. Metals may be selected based on a variety of factors, such as conductivity and tensile strength. Thus, although stainless steel has lower conductivity than copper and/or gold, it provides the strength required to puncture tissue and/or skin. In such cases, the inner and outer conductors 20 and 24 may be plated with conductive material (e.g., copper, gold, etc.) to improve conductivity and/or decrease energy loss.

Figure 3A:
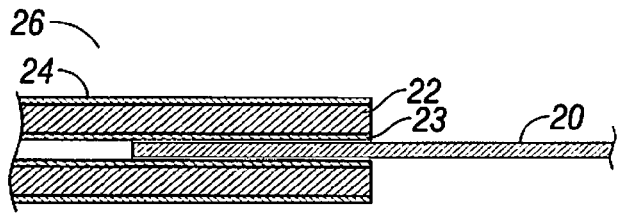
FIGS. 3A-C are side cross-sectional views of the microwave ablation probe of FIG. 2.

In one embodiment, the feedline 26 includes a secondary inner conductor 23, as shown in FIG. 3A, having a tubular structure which surrounds the inner conductor 20. The inner conductor 20 is slidably disposed within the secondary inner conductor 23 (e.g., moves within the secondary inner conductor 23 while maintaining smooth continuous contact therewith), such that the inner conductor 20 can be slid in either the proximal and/or distal direction to tune the inner conductor 20 to a desired operational frequency. The inner conductor 20 and the secondary inner conductor 23 are in electromechanical contact, allowing the inner conductor 20 to slide in and out of the feedline 26 during tuning while continuing to conduct microwave energy.

Figure 3B:
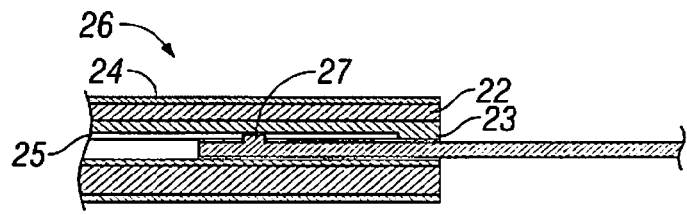

As shown in FIG. 3B, the feedline 26 includes one or more grooves 25 which mechanically interface with one or more corresponding stop members 27 disposed on the inner conductor 20. The groove 25, may be disposed in the secondary inner conductor 23 and/or the insulative spacer 22. The groove 25 in conjunction with the corresponding stop member 27, guides and limits the movement of the inner conductor 20 as the inner conductor 20 is slid within the feedline 26. Further, the groove 25 and stop member 27 combination provides for additional conductive contact between the secondary inner conductor 23 and the inner conductor 20. In embodiments, the location of the groove 25 and the stop member 27 may be interchanged, such that the groove 25 may be disposed within the inner conductor 20 and the stop member 27 may be disposed on the secondary inner conductor 23.

With reference to FIG. 2, the choke 28 of the probe 12 is disposed around the feedline 26 and includes an inner dielectric layer 32 and an outer conductive layer 34. The choke 28 confines the microwave energy from the generator 14 to the radiating portion 30 of the probe 12 thereby limiting the microwave energy deposition zone length along the feedline 26. The choke 28 is implemented with a quarter wave short by using the outer conductive layer 34 around the outer conductor 24 of the feedline 26 separated by the dielectric layer 32. The choke 28 is shorted to the outer conductor 24 of the feedline 26 at the proximal end of the choke 28 by soldering or other means. In embodiments, the length of the choke 28 may be from a quarter to a full wavelength. The choke 28 acts as a high impedance to microwave energy conducted down the outside of the feedline 26 thereby limiting energy deposition to the end of the probe. In one embodiment, the dielectric layer 32 is formed from a fluoropolymer such as tetrafluorethylene, perfluorpropylene, and the like and has a thickness of 0.005 inches. The outer conductive layer 34 may be formed from a so-called "perfect conductor" material such as a highly conductive metal (e.g., copper).

Figure 3C:
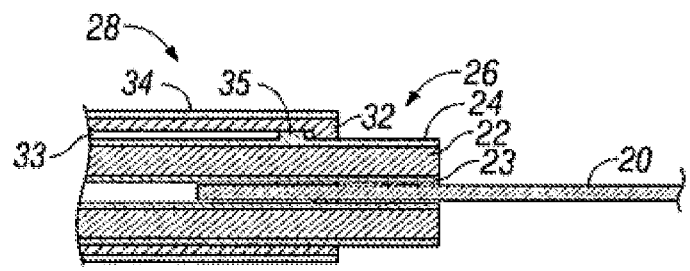

As shown in FIG. 3C, the choke 28 is configured to slide atop the feedline 26 along the longitudinal axis defined by the probe 12. Sliding the choke 28 in either proximal and/or distal direction along the feedline 26 provides for adjustment of the length of the radiating portion 30. The choke 28 includes a groove 33 disposed within the dielectric layer 32. The groove 33 is configured to mechanically interface with a stop member 35 that is disposed on the outer conductor 24. The stop member 35 guides the sliding of the choke 28 along the length of the groove 33.

Moving one or both of the inner conductor 20 and the choke 28 relative to the feedline 26 allows for adjustment of the length of the radiating portion 30, such as adjusting the choke 28 and the inner conductor 20 to be ¼ wavelength long as the ablation continues to maintain ½ wavelength dipole. In embodiments, the inner conductor 20, the feedline 26 and the choke 28 may have markings and/or indicia thereon to indicate desired wavelength adjustment positions.

In one embodiment, the grooves 25 and 33 and/or the stop members 27 and 35 may include one or more detents (not explicitly shown) which provide tactile feedback when the choke 28 and/or inner conductor 20 are slid along the feedline 26. This allows for more precise movement of the components and tuning of the radiating portion 30.

The probe 12 further includes a tapered end 36 which terminates in a tip 38 at the distal end of the radiating portion 30. The tapered end 36 allows for insertion of the probe 12 into tissue with minimal resistance. In cases where the radiating portion 12 is inserted into a pre-existing opening, the tip 38 may be rounded or flat. The tapered end 36 may be formed from any hard material such as metal and/or plastic.

Figure 4:
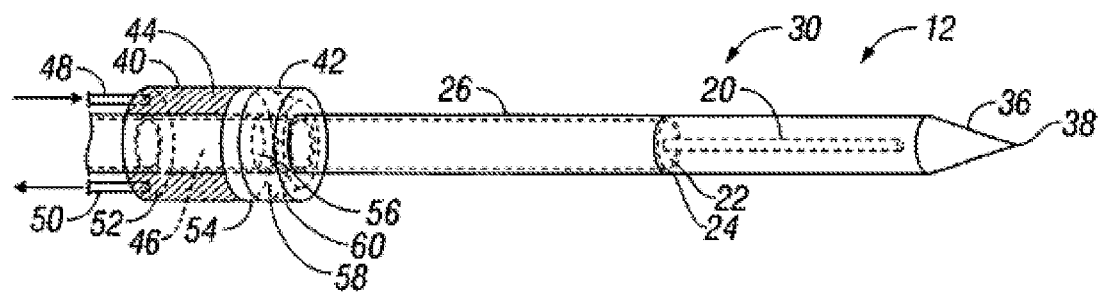
FIG. 4 is a perspective cross-sectional view of the microwave ablation probe having liquid cooled choke according to the present disclosure.

FIG. 4 shows another embodiment of the probe 12 having a liquid-cooled choke 40 that includes a cylindrical conducting housing 42 having a chamber 44 and defining a cylindrical cavity 46 which surrounds the feedline 26. The housing 42 is formed from a conducting metal such as copper, stainless steel, and/or alloys thereof. The housing 42 includes one or more inlet tubes 48 and outlet tubes 50 which cycle a cooling dielectric liquid 52 (e.g., water, saline solution, and the like) through the chamber 44. The liquid 52 may be supplied by a pump (not explicitly shown) configured to adjust the flow rate of the liquid 52 through the chamber 44. As the liquid 52 is supplied into the choke 40, the heat generated by the feedline 26 is removed. Further, compounds used in the liquid 52 may be adjusted to obtain a desired dielectric constant within the choke 28. This may be useful in multi-frequency probes allowing the resonant frequency of the choke 28 to be adjusted by filling the chamber 44 with varying fluid volume and/or varying the ratio of air and liquid therein.

The housing 42 also includes an O-ring 54 having an opening 56 allowing the O-ring 54 to fit within the chamber 44. As the chamber 44 is filled with the liquid 52, the liquid 52 pushes the O-ring 54 in the distal direction within the chamber 44. The O-ring 54 fits the walls of the chamber 44 in a substantially liquid-tight fashion preventing the liquid 52 from seeping into a distal portion 58 of the chamber 44. This allows selective or automatic adjustment of the cooling temperature of the choke 28 by limiting the volume of the chamber 44 being filled with the liquid 52.

More specifically, the O-ring 54 is formed from rubber, silicone rubber and other elastomer material such that the frictional forces between the O-ring 54 and the housing 42 maintain the O-ring 54 in position until the flow rate of the liquid 52 is sufficient to shift the O-ring 54 in the distal direction. In one embodiment, the distal portion 58 includes sloping or chamfered walls 60 inside the chamber 44. As the O-ring 54 is pushed in the distal direction, the sloping walls 60 compress the O-ring 54 which requires an increase in the flow rate of the liquid 52. This provides for a counter-force that pushes back against the flow of the liquid 52 requiring an increase in the flow rate if additional filling of the chamber 44 (e.g., additional cooling of the choke 28) is desired. Once the liquid 52 is withdrawn from the choke 28, the O-ring 54 is moved back into its original position (e.g., in the proximal direction) by the compression of the walls 60.

Figure 5:
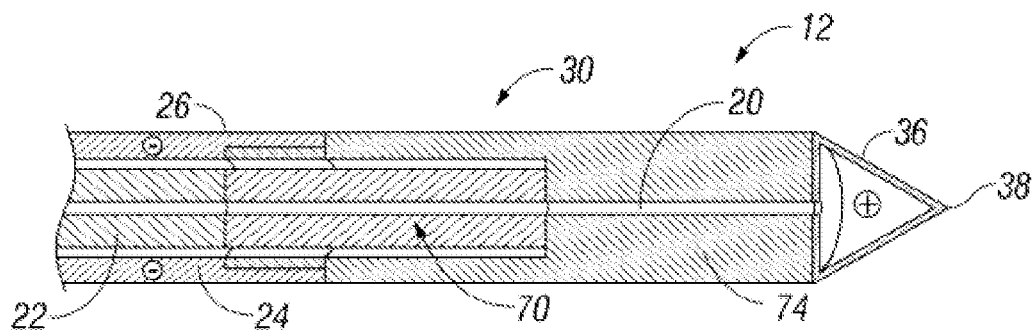
FIG. 5 is a perspective cross-sectional view of one embodiment of the microwave ablation probe having a thermally reactive dielectric material therein according to the present disclosure.

FIG. 5 shows a further embodiment of the probe 12 having a ferroelectric material therein. More specifically, the probe 12 includes an internal ferroelectric loading 70 at a distal end of the feedline 26 and an external ferroelectric loading 74 at the distal end of the inner conductor 20. In one embodiment, the internal ferroelectric loading 70 may be have a length corresponding to the quarter wave of the microwave frequency and act as a dynamic quarter-wave transformer.

The ferroelectric loadings 70 and 74 include ferroelectric material such as lead zirconate, lead titanate, barium titanate, and the like. Ferroelectric materials provide for dynamic matching of the probe 12 to the tissue due to changing dielectric properties of such materials when DC electric field is applied across thereof during application of microwave energy to the probe 12 such that the DC electric field biases the ferroelectric material. The DC electric field is supplied to the loadings 70 and 74 through the outer conductor 24 and inner conductor 20 respectively. As the DC electric field is supplied to the loadings 70 and 74, the dielectric constant thereof is varied. The "+" and "−" illustrate one possible polarity of DC electric field within the probe 12. As the wavelength of the frequency of operation increases due to desiccation of the tissue, the DC electric field is supplied to the loadings 70 and 74 is also adjusted accordingly to increase the dielectric constant accordingly. This counteracts the claiming of the probe 12 due to the changes in the tissue. In one embodiment, the DC electric field supply (not explicitly shown) may be controlled via a feedback loop by the generator 14 based on impedance measurement of the probe 12 and the cable 16 and other methods within purview of those skilled in the art. In another embodiment, the supply of the DC current may be varied in a predetermined fashion over time based on empirical laboratory measurements.

The described embodiments of the present disclosure are intended to be illustrative rather than restrictive, and are not intended to represent every embodiment of the present disclosure. Various modifications and variations can be made without departing from the spirit or scope of the disclosure as set forth in the following claims both literally and in equivalents recognized in law.

What is claimed is:

1. A microwave ablation probe for providing microwave energy to tissue, the microwave ablation probe comprising:
    a feedline including an inner conductor, a secondary inner conductor, an insulating spacer, and an outer conductor, the inner conductor being longitudinally movable relative to the secondary inner conductor while maintaining electro-mechanical contact therewith;
    a radiating portion including at least a portion of the inner conductor centrally disposed within the radiating portion; and
    a choke disposed around at least a portion of the feedline and configured to confine the microwave energy to the radiating portion, the choke including a conductive housing having a chamber for storing a cooling dielectric liquid.

2. The microwave ablation probe according to claim 1, wherein the choke includes at least one inlet tube and at least one outlet tube configured to supply the cooling dielectric liquid into the chamber.

3. The microwave ablation probe according to claim 1, wherein the choke includes an O-ring slidably disposed within the chamber, such that when the cooling dielectric liquid is supplied thereto the O-ring is moved in a distal direction.

4. The microwave ablation probe according to claim 1, wherein the cooling dielectric liquid is selected from the group consisting of water and saline solution.

5. The microwave ablation probe according to claim 1, further including a tapered end having a tip disposed at a distal end of the radiating portion.

6. A microwave ablation probe for providing microwave energy to tissue, the microwave ablation probe comprising:
    a feedline including an inner conductor, a secondary inner conductor, an insulating spacer, and an outer conductor, the inner conductor being longitudinally movable relative to the secondary inner conductor while maintaining electro-mechanical contact therewith;

a radiating portion including at least a portion of the inner conductor centrally disposed within the radiating portion; and at least one loading including a direct current electric field-dependent dielectric material, wherein at least one dielectric property of the direct current electric field-dependent dielectric material varies in response to the DC electric field supplied thereto.

7. The microwave ablation probe according to claim 6, further including:

a tapered end having a tip disposed at a distal end of the radiating portion.

8. The microwave ablation probe according to claim 6, wherein the direct current electric field-dependent dielectric material is a ferroelectric material selected from the group consisting of lead zirconate, lead titanate and barium titanate.

9. The microwave ablation probe according to claim 6, further comprising:

an internal loading disposed at a distal end of the feedline; and an external loading disposed at a distal end of the inner conductor.

10. The microwave ablation probe according to claim 9, wherein the internal loading is a dynamic quarter-wave transformer.

11. The microwave ablation probe according to claim 9, wherein the internal loading is of a first polarity and the external loading is of a second polarity.

* * * * *